United States Patent [19]

DeSantis et al.

[11] Patent Number: 4,822,820
[45] Date of Patent: Apr. 18, 1989

[54] USE OF TRI-METHYL PG-$F_2A$ AND DERIVATIVES IN GLAUCOMA THERAPY

[75] Inventors: Louis M. DeSantis, Fort Worth; Verney L. Sallee, Southlake, both of Tex.

[73] Assignee: Alcon Laboratories, Inc., Fort Worth, Tex.

[21] Appl. No.: 933,841

[22] Filed: Nov. 24, 1986

[51] Int. Cl.[4] .................. A61K 31/215; A61K 31/19; A61K 31/557
[52] U.S. Cl. .................................... 514/530; 514/573; 514/913
[58] Field of Search ........................ 514/530, 573, 913

[56] References Cited

U.S. PATENT DOCUMENTS

| | | | |
|---|---|---|---|
| 4,004,027 | 1/1977 | Lippmann et al. | 514/573 |
| 4,029,681 | 6/1977 | Smith | 260/408 |
| 4,070,482 | 1/1978 | Lippmann et al. | 514/573 |
| 4,097,496 | 6/1978 | Babej et al. | 514/530 |
| 4,112,225 | 9/1978 | Holland et al. | 542/426 |
| 4,288,616 | 9/1981 | Sih | 562/503 |
| 4,311,707 | 1/1982 | Bimbaum et al. | 514/573 |
| 4,564,637 | 1/1986 | Schachar | 514/573 |
| 4,599,353 | 7/1986 | Bito | 514/530 |

OTHER PUBLICATIONS

Chemistry, Biochemistry & Pharmacological Activity of Prostanoids-pp. 1, and 4–1978–Gorton.
Chem. Abst. 71:120112(a) (1969)–Beitch et al.
Chem. Abst. 78:80097(k) (1973)–Nakano et al.
Chem. Abst. 80:44231(g) (1974)–Chiang.
Chem. Abst. 81:21424(d) (1974)–Chiang.
Chem. Abst. 81:45653(d) (1974)–Masuda et al.
Chem. Abst. 102:16111(b) (1985)–Trzeciakowski et al.

*Primary Examiner*—Douglas W. Robinson
*Attorney, Agent, or Firm*—James A. Arno; Gregg C. Brown

[57] ABSTRACT

Disclosed is the use of Tri-methyl PG-$F_2a$, and its derivatives, such as, 15-acetyl Tri-methyl PG-$F_2a$ and pharmaceutically acceptable esters thereof in the treatment of glaucoma and intraocular hypertension. Also disclosed are ophthalmic pharmaceutical compositions comprising Tri-methyl PG-$F_2a$ and its derivatives.

1 Claim, No Drawings

USE OF TRI-METHYL PG-F₂A AND DERIVATIVES IN GLAUCOMA THERAPY

BACKGROUND OF THE INVENTION

This invention relates to the use of Tri-methyl PG-F2a and its derivatives (I) in the treatment of glaucoma and ocular hypertension.

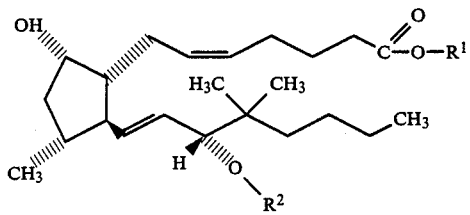

wherein $R^1$ is hydrogen, a cationic salt moiety, a pharmaceutically acceptable amine moiety or a pharmaceutically acceptable ester moiety derived from the corresponding alcohol; and $R^2$ is hydrogen or a pharmaceutically acceptable ester moiety derived from the corresponding carboxylic acid.

Natural prostaglandins are known to lower intraocular pressure (IOP) after topical ocular instillation, but can cause an inflammatory response. Many synthetic prostaglandins have been observed to lower intraocular pressure, but most such compounds also produce the described inflammatory response. Unexpectedly, the 11-alpha methyl group on an E-series prostaglandin analog was shown to essentially eliminate the inflammatory response but maintain a reasonable level of IOP reducing activity. Since it has also been shown that F-series prostaglandins have a greater potency for IOP reduction than E-series prostaglandins, the extension of the utility of the 11-alpha methyl group is reasonable and appropriate. Compounds of I are known.

DETAILED DESCRIPTION OF THE INVENTION

The compounds of the present invention (I) are known. See, for example, U.S. Pat. No. 4,112,225, which is incorporated herein by reference to the extent that it describes the preparation and known pharmacological profile of I.

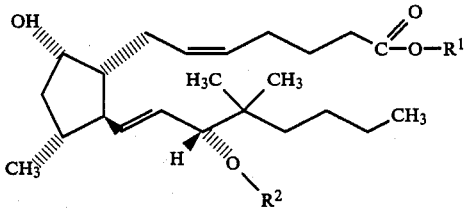

wherein $R^1$ is hydrogen or a pharmaceutically acceptable salt or ester and $R^2$ is hydrogen or a pharmaceutically acceptable ester moiety.

By "pharmaceutically acceptable salts and esters", as used herein, is meant esters and salts of Tri-methyl PG-F₂a which have the same general pharmacological properties as the acid form from which they are derived, and which are acceptable from a toxicity viewpoint.

Specifically included in this term are salts and esters of the type disclosed in U.S. Pat. No. 4,029,681, issued June 19, 1977 and in U.S. Pat. No. 4,288,616, issued Sept. 8, 1981, the disclosures of which are incorporated herein by reference. Preferred esters are $C_1$–$C_{12}$ alkyl esters, straight or branched, particularly methyl, ethyl, isopropyl and iso- or tert-butyl. Preferred salts are the alkali and alkaline earth metal salts, in particular sodium and potassium, ammonium, and amine salts, in particular tris(hydroxymethyl)aminomethane salt.

With respect to the identity of $R^1$ and $R^2$ in Structure I, esters contemplated for the compounds of the invention include any ester moiety which permits the compound to retain its pharmaceutical use in lowering intraocular pressure, and provides a compound which is safe and effective. Thus the compounds covered by the above general formula include the free acid (—COOH, $R^1$=H), and alcohol (—OH, $R^2$=H), alkali and alkaline earth metal salts (e.g., Na, K, Ca, and Mg), ammonium and amine salts and esters. The invention is inclusive of all ester radicals, $R^1$ and $R^2$, known to be effective as pharmaceutically acceptable esters. Lower alkyl esters are especially preferred.

In a more preferred embodiment, $R^1$ and $R^2$, which may be the same or different, are hydrogen or alkyl esters wherein the alkyl group is methyl, ethyl, propyl, isopropyl, cyclopropyl, cyclopropylmethyl, butyl, cyclobutyl, isobutyl, t-butyl, or pentyl.

Alkali metal salts and alkaline earth metal salts of the acid form of I may be formed conventionally. The alcohol and/or acid or salt may be subsequently esterified with the appropriate acid and/or alcohol, e.g., a $C_1$ to $C_5$ alkyl alcohol to yield the final ester product embodiment of I according to know procedures.

In a similar manner other esterifications may be effected as is known in the art employing other lower alkyl, cycloalkyl, cycloalkylalkyl, aryl, or arylalkyl alcohols and/or acids such as isopropanol, cyclopropanol, cyclopropylmethanol, phenyl, or benzyl alcohol. Since such esterification reactions are well known, they are not further described here.

The compounds of the present invention are useful in lowering intraocular pressure and thus are useful in the treatment of glaucoma. The compounds are essentially devoid of unwanted side effects such as marked vasoconstriction or vasodilation of the vessels of the sclera, painful stinging and intraocular inflammation.

The compounds are preferably administered topically. The dosage range is 0.001 to 1.0 mg per eye. The compounds of the present invention can be administered as solutions, suspensions, or emulsions (dispersions) in a suitable ophthalmic vehicle.

In forming compositions for topical administration, the compounds are preferably formulated as 0.01 to 2.0 percent by weight solutions in water at a pH of 4.5 to 8.0. While the precise regimen is left to the discretion of the clinician, it is recommended that the resulting solution be topically applied by placing one drop in each eye two times a day.

Other ingredients which may be desirable to use in the ophthalmic preparations of the present invention include preservatives, cosolvents and viscosity builder agents.

ANTIMICROBIAL PRESERVATIVE

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Typically such preservatives are employed at a level of from 0.001% to 1.0% by weight.

CO-SOLVENTS

Prostaglandin and particularly ester derivatives typically have limited solubility in water, therefore may require a surfactant or other appropriate co-solvent in the composition. Such cosolvents include polysorbate 20, 60 and 80, Pluronic F-68, F-84 and P-103, cyclodextrin, or other agents known to those skilled in the art. Typically such co-solvents are employed at a level of from 0.01% to 2% by weight.

VISCOSITY AGENTS

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity builder agents include as examples polyvinyl alcohol, polyvinyl, pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The following examples are representative pharmaceutical compositions of the invention are topical use in lowering of intraocular pressure. The active prostaglandin is designated as I (from structure I, above) with values for $R^1$ and $^2$ shown.

| Ingredient | Percentage by Weight |
|---|---|
| Example A | |
| I,$R^1$=Isopropyl,$R^2$=H | 0.05 |
| Benzalkonium chloride | 0.01 |
| Polysorbate 80 | 0.05 |
| Sodium acetate | 0.07 |
| Sodium chloride | 0.6 |
| Hydroxypropyl methyl cellulose | 0.5 |
| hydrochloric acid and/or | to adjust pH to 5.0 |
| sodium hydroxide | to 5.5 |
| Purified Water | q.s. to 100% |
| Example B | |
| I,$R^1$=H, $R^2$=acetyl | 0.1 |
| Benzalkonium chloride | 0.01 |
| Pluronic P-84 | 0.5 |
| Dried sodium phosphate | 0.01 |
| Sodium biphosphate | 0.07 |
| Sodium chloride | 0.18 |
| Sodium hydroxide and/or hydrochloric acid | to adjust Ph |
| Purified Water | q.s. to 100% |
| Example C | |
| I,$R^1$=isopropyl, $R^2$=acetyl | 0.05 |
| Chlorobutanol | 0.5 |
| Sodium acetate | 0.14 |
| Disodium edetate | 0.01 |
| Sodium chloride | 0.52 |
| Hydrochloric acid and/or sodium hydroxide | to adjust pH |
| Polyvinyl alcohol | 1.0 |
| Purified Water | q.s. to 100% |

The invention has been described herein by reference to certain preferred embodiments. However, as obvious variations thereon will become apparent to those skilled in the art, the invention is not to be considered as limited thereto.

What is claimed is:

1. A method of treating glaucoma and ocular hypertension which comprises applying topically to the affected eye an ophthalmic composition containing a therapeutically effective amount of a compound of formula:

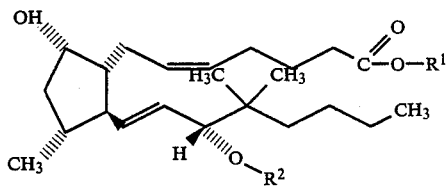

wherein:
R1 is selected from hydrogen, an alkali metal cation, and alkyl having 1 to 6 carbon atoms; and R2 is selected from hydrogen and alkyl having 1 to 6 carbon atoms.

* * * * *